United States Patent [19]
Walling

[11] Patent Number: 5,460,594
[45] Date of Patent: Oct. 24, 1995

[54] INTERFACE PLATE

[76] Inventor: Allan J. Walling, 3000 Candide, McKinney, Tex. 75070

[21] Appl. No.: 193,438
[22] Filed: Feb. 8, 1994
[51] Int. Cl.⁶ ................................................ A61F 5/00
[52] U.S. Cl. ............................................ 600/38; 600/41
[58] Field of Search ...................................... 600/38–41

[56] References Cited

U.S. PATENT DOCUMENTS

| | | |
|---|---|---|
| 3,361,853 | 1/1972 | Burdette, Jr. . |
| 3,636,948 | 1/1972 | Atchley . |
| 3,744,486 | 7/1973 | Wilson . |
| 4,175,554 | 11/1979 | Gerow . |
| 4,203,432 | 5/1980 | Koch . |
| 4,378,008 | 3/1983 | Osbon, Sr. . |
| 4,539,980 | 9/1985 | Chaney . |
| 4,638,915 | 12/1986 | Chaney . |
| 4,643,175 | 2/1987 | Chapman . |
| 4,718,411 | 1/1988 | Stewart . |
| 4,722,327 | 2/1988 | Harvey . |
| 4,723,538 | 2/1988 | Stewart et al. . |
| 4,741,329 | 5/1988 | Marcune . |
| 4,753,227 | 6/1988 | Yanuck, Jr. . |
| 4,834,115 | 5/1989 | Stewart . |
| 4,856,498 | 8/1989 | Osbon . |
| 4,856,499 | 8/1989 | Kelly . |
| 4,967,738 | 11/1990 | March . |
| 4,995,381 | 2/1991 | Marmar et al. . |
| 5,085,209 | 2/1992 | Gottschalk . |
| 5,125,890 | 6/1992 | Merrill et al. ........................ 600/39 |
| 5,195,943 | 3/1993 | Chaney . |
| 5,213,563 | 5/1993 | Cox . |
| 5,221,251 | 6/1993 | Edminster . |
| 5,234,401 | 8/1993 | Yamanaka . |
| 5,234,402 | 8/1993 | Osbon . |
| 5,344,389 | 9/1994 | Walsdorf et al. ...................... 600/41 |

FOREIGN PATENT DOCUMENTS 9117727  11/1991  WIPO ...................................... 600/41

OTHER PUBLICATIONS

Frank T. Salvatore, George M. Sharman, Wayne J. G. Hellstrom, "Vacuum Constriction Devices and the Clinical Urologist: An Informed Selection", Urology, Oct. 1991, vol. XXXVIII, No. 4, pp. 323–327; Stanley G. Korenman. Sharon P. Viosca, Fran E. Kaiser, Arshaq D. Mooradian, and John E. Morely, "Use of a Vacuum Tumescence Device in the Mangagement of Impotence", JAGS, Mar. 1990, vol. 38, No. 3, pp. 217–220.

Primary Examiner—Lee S. Cohen
Assistant Examiner—M. Lacyk
Attorney, Agent, or Firm—Daniel V. Thompson

[57] ABSTRACT

An interface plate for a vacuum constriction device used with an elastic constriction ring includes an interface plate member. The interface plate member has an inner cylindrical wall with an open, circular end. The end intersects a planar backup surface perpendicular to the inner wall, such that the end defines a circular aperture in the backup surface. The circular aperture is of selected dimension to prevent the formation of undesired abdominal and/or scrotal bulges past an elastic constriction ring when vacuum is applied to the vacuum constriction device.

12 Claims, 2 Drawing Sheets

INTERFACE PLATE

FIELD OF THE INVENTION

The present invention relates to therapeutic devices, and in particular to devices for vacuum tumescence therapy.

REFERENCE TO DISCLOSURE DOCUMENT

Reference is hereby made to Disclosure Document No. 344,070, received Dec. 6, 1993.

BACKGROUND ART

Approximately ten percent of the adult male population suffers from some degree of erectile dysfunction. A number of treatment methods are known, and the use of vacuum constriction devices is considered to be the least invasive and most successful of the non-medical therapies available. The principle underlying vacuum tumescence therapy is that a satisfactory erection can be produced by way of a vacuum chamber or cylinder which draws blood into the corporeal bodies. The erection is maintained by placement of an elastic constriction ring adjacent the abdomen. The cylinder is then removed providing a satisfactory erectile state until the ring is removed.

A substantial drawback of the vacuum constriction device method of therapy is that an estimated 30 to 40 percent of potential users experience the problem of abdominal and/or scrotal bulges. Problems of this nature are caused by a bulge of loose abdominal tissue being drawn into the cylinder when vacuum is applied and then entrapped when the ring is applied. Alternatively, the similar problem of scrotal bulge results from a portion of the scrotal tissue being drawn into the cylinder and then entrapped. Of the 30 to 40 percent of users experiencing this problem, approximately half simply cannot use this type of therapy due to bulge problems. The remaining half are able to use the therapy, but the results are less than entirely satisfactory.

Thus, there presently exists a need for preventing the formation of abdominal and scrotal bulges in vacuum tumescence therapy.

SUMMARY OF THE INVENTION

The present invention provides an interface plate for a vacuum constriction device used with an elastic constriction ring. The interface plate includes a planar backup surface of selected dimension. Ring retainer means cooperates with the backup surface to prevent the formation of abdominal and scrotal bulges past an elastic constriction ring when vacuum is applied to the vacuum constriction device.

BRIEF DESCRIPTION OF THE DRAWINGS

A more complete understanding of the invention and its advantages will be apparent from the Detailed Description taken in conjunction with the Drawings, in which.

DETAILED DESCRIPTION OF THE PREFERRED EMBODIMENT

Figure 1:
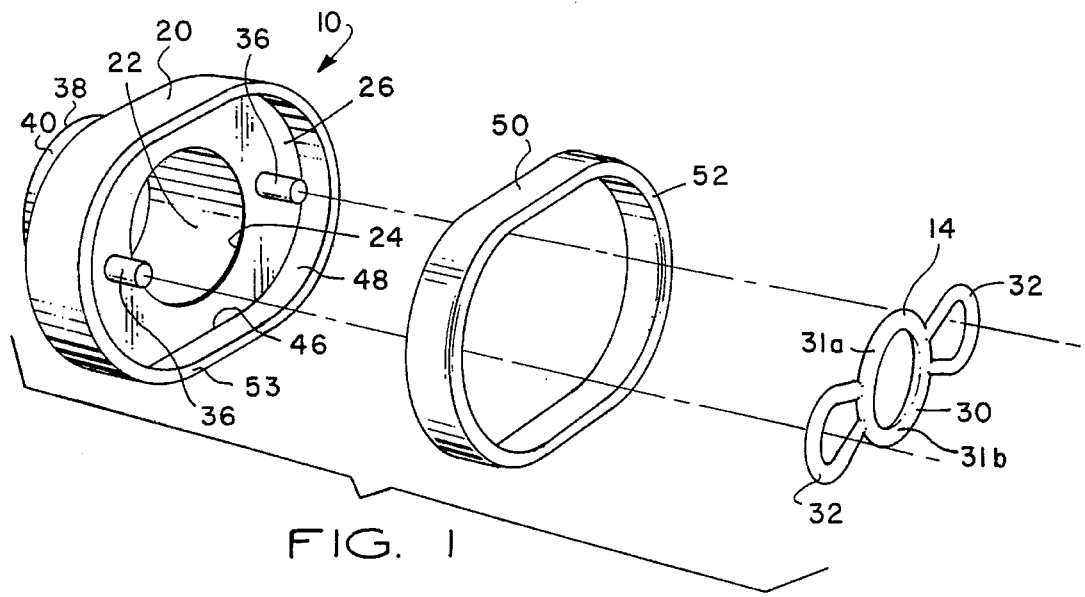
FIG. 1 is an exploded, perspective view of an interface plate constructed in accordance with the invention and an elastic constriction ring.
Figure 2:
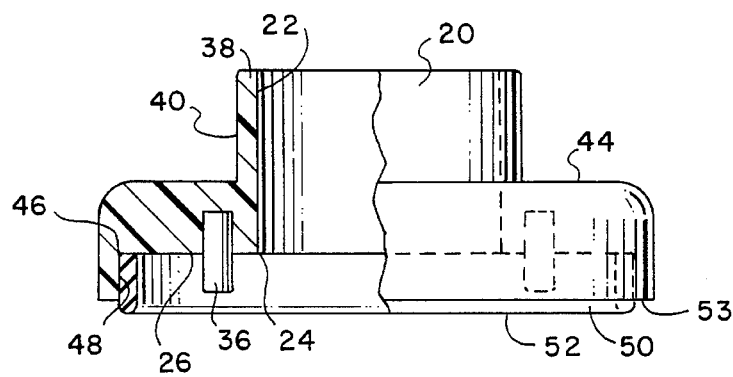
FIG. 2 is a partially broken away top view of the interface plate of FIG. 1.
Figure 3:
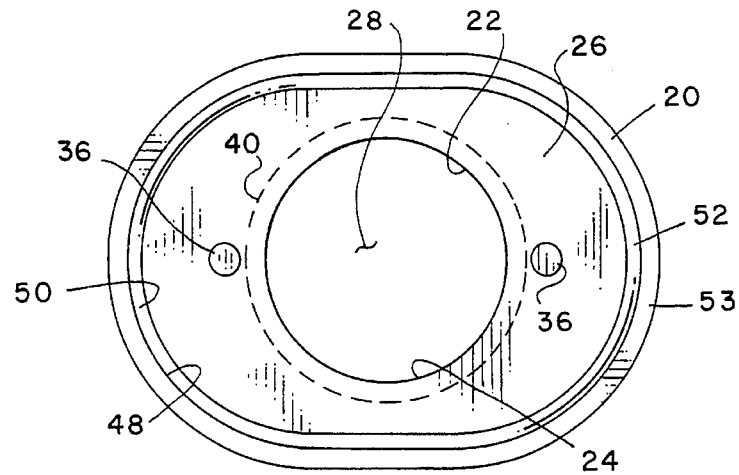
FIG. 3 is a front view of the interface plate of FIG. 1.

Referring to FIGS. 1–5, where like numerals refer to like and corresponding elements, an interface plate 10 is adapted for use with a vacuum constriction device 12 and an elastic constriction ring 14. As explained above, vacuum constriction device 12 is typically usable without any bulge problem for the majority of users. Therefore, interface plate 10 is preferably an optional add-on device to be used only when necessary. It will be understood, however, that interface plate 10 may be formed as an integral part of the vacuum constriction device 12 without departing from the scope of this invention.

Interface plate 10 includes an interface plate member 20 formed of a rigid material such as injection-molded thermoplastic. Interface plate member 20 has an inner wall 22 having an open, circular first end 24, with inner wall 22 being cylindrical. First end 24 intersects a planar backup surface 26 perpendicular to inner wall 22, such that first end 24 defines a circular aperture 28 (FIG. 3) in backup surface 26.

Figure 4:
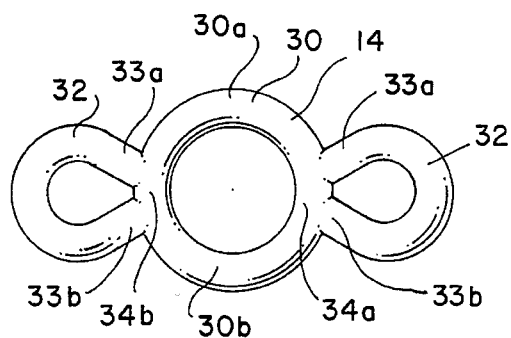
FIG. 4 is a front view of an elastic constriction ring adapted for use with the present invention.
Figure 6:
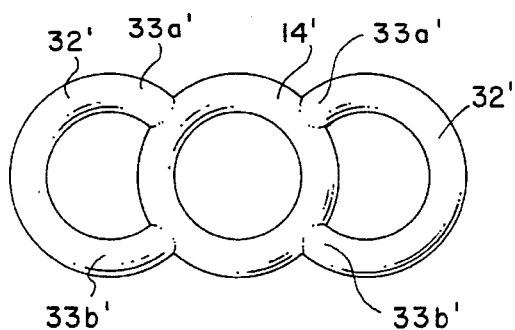
FIG. 6 is a front view of a prior art elastic constriction ring.

FIG. 4 illustrates an elastic constriction ring 14 specially adapted for use with the present invention. Ring 14 has a central section 30 and two peripheral loops 32. Central section 30 has an upper portion 30a and a lower portion 30b. Loops 32 have closely-spaced ends 33a, 33b that join central section 30 at sides 34a, 34b of central section 30. In contrast, the prior art elastic constriction ring 14' (FIG. 6) had loops 32' having widely-spaced ends 33a', 33b'.

In the preferred embodiment, retainer means includes two ring retainer pegs 36 extending from backup surface 26 and adapted to hold peripheral loops 32 of restriction ring 14. Preferably, the ring retainer pegs 36 are cylinders molded in interface plate member 20 at locations diametrically opposed about circular aperture 28.

Figure 5:
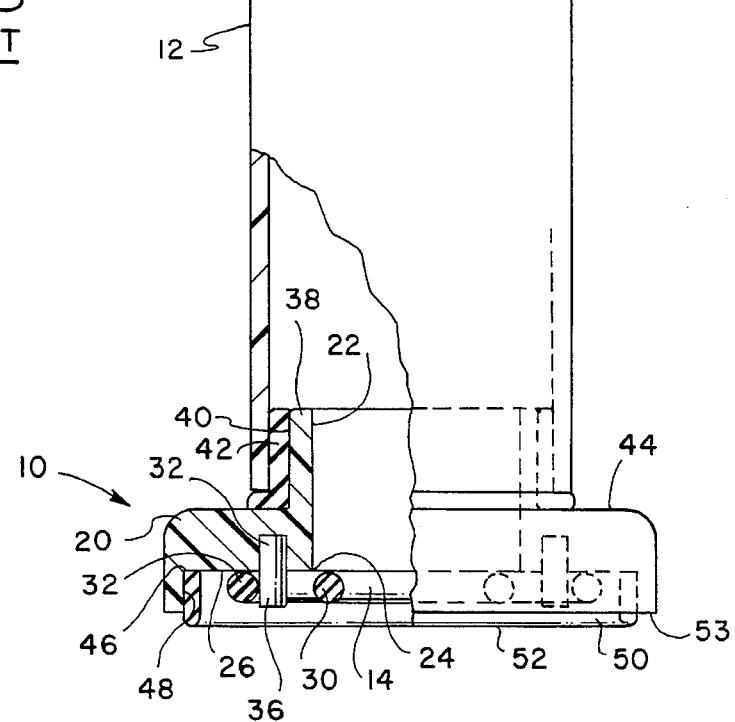
FIG. 5 is a partially broken away top view of an interface plate and an elastic constriction ring interfitted with a vacuum constriction device.

Inner wall 22 has an open, circular second end 38. Interface plate member 20 also has a cylindrical outer wall 40, and the outer wall 40 is coaxial with inner wall 22. Outer wall 40 is sized to sealingly interfit with vacuum constriction device 12, by way of resilient seal 42, as best shown in FIG. 5. Interface plate member 20 is provided with a planar outer surface 44 extending from and perpendicular to outer wall 40. Planar outer surface 44 is adapted to axially fix interface plate member 20 with respect to vacuum constriction device 12.

Backup surface 26 has a capsule-shaped outer perimeter 46, with a seal-retaining wall 48 extending perpendicularly about backup surface perimeter 46. A resilient seal 50 is interfitted with seal-retaining wall 48, and seal 50 has a sealing surface 52 extending forwardly from forward wall 53. Seal-retaining surface 48 terminates at forward wall 53. Forward wall 53 may be planar, as shown, or may be slightly curved to aid in sealing against the abdomen.

In operation, ring 14 is first stretched to fit over the end of vacuum constriction device 12, before interface plate 10 is interfitted. Ring 14 is then slipped off the end of vacuum constriction device 12 at its proper location at the base of the penis adjacent the abdomen. Next, interface plate 10 is interfitted with the end of vacuum constriction device 12 to form a combination assembly. The assembly is then placed into position, and loops 32 are slipped over ring retaining pegs 36. When vacuum is applied, the loops 32, with closely-spaced ends 33a, 33b, and pegs 36 prevent ring 14 from being drawn into the cylinder, and as increasing tension is placed on loops 32 the upper and lower portions 30a, 30b of central section 30 are drawn together as a result of the loops 32 having closely-spaced ends 33a, 33b. If the ends 33a, 33b were widely-spaced, as in the prior art (FIG. 6), the overall opening of central section 30' would be increased, having the opposite effect of encouraging bulges. As vacuum increases, as well as the tension on loops 32, the upper and lower portions 30a, 30b of central section 30 apply extra pressure as they are drawn together to prevent the formation of bulges. After application of sufficient vacuum, vacuum is released and the assembly is removed.

Thus it can be seen that the retainer means in cooperation with the backup surface allows internal fluids to be drawn past elastic ring 14, but tissue is prevented from such passage.

Whereas the present invention has been described with respect to a specific embodiment thereof, it will be understood that various changes and modifications will be suggested to one skilled in the art, and it is intended to encompass such changes and modifications as fall within the scope of the appended claims.

I claim:

1. An interface plate for a vacuum constriction device used with an elastic constriction ring, comprising:

an interface plate member;

said interface plate member having an inner wall;

said inner wall being cylindrical and having an open, circular first end;

said first end intersecting a planar backup surface perpendicular to said inner wall, such that said first end defines a circular aperture in said backup surface; and ring retainer means adapted to hold an elastic constriction ring, said retainer means cooperating with said circular aperture to prevent the formation of abdominal and scrotal bulges past the elastic constriction ring when vacuum is applied to the vacuum constriction device.

2. The interface plate of claim 1 wherein said ring retainer means includes at least one ring retainer peg extending from said backup surface and adapted to hold an elastic constriction ring.

3. The interface plate of claim 2 having two said ring retainer pegs diametrically opposed about said circular aperture.

4. The interface plate of claim 1 wherein said interface plate member is a unitary body separate from the vacuum constriction device and adapted to interfit with the vacuum constriction device.

5. The interface plate of claim 1 wherein said inner wall has an open, circular second end, and said interface plate member has a cylindrical outer wall, said outer wall being coaxial with said inner wall and sized to sealingly interfit with the vacuum constriction device.

6. The interface plate of claim 5 with a planar outer surface extending from and perpendicular to said cylindrical outer wall, said planar outer surface being adapted to axially fix said interface plate member with respect to the vacuum constriction device.

7. The interface plate of claim 1 wherein said backup surface has a capsule-shaped outer perimeter.

8. The interface plate of claim 7 with a seal-retaining wall extending perpendicularly about said backup surface perimeter.

9. The interface plate of claim 8 further including a resilient seal interfitted with said seal-retaining wall.

10. The interface plate of claim 9 with said seal-retaining surface terminating at a forward wall, and said seal having a sealing surface extending forwardly of said forward wall.

11. An interface plate for a vacuum constriction device used with an elastic constriction ring, comprising:

an interface plate member;

said interface plate member having an inner wall;

said inner wall having an open, circular first end and being cylindrical;

said first end intersecting a planar backup surface perpendicular to said inner wall, such that said first end defines a circular aperture in said backup surface;

ring retainer means adapted to hold an elastic constriction ring, said retainer means cooperating with said circular aperture to prevent the formation of abdominal and scrotal bulges past the elastic constriction ring when vacuum is applied to the vacuum constriction device;

said ring retainer means including two ring retainer pegs extending from said backup surface and adapted to hold an elastic constriction ring;

said ring retainer pegs being cylinders fixed in said interface plate member at locations diametrically opposed about said circular aperture;

said interface plate member being a unitary body separate from the vacuum constriction device and adapted to interfit with the vacuum constriction device;

wherein said inner wall has an open, circular second end, and said interface plate member has a cylindrical outer wall, said outer wall being coaxial with said inner wall and sized to sealingly interfit with the vacuum constriction device;

with a planar outer surface extending from and perpendicular to said cylindrical outer wall, said planar outer surface being adapted to axially fix said interface plate member with respect to the vacuum constriction device;

wherein said backup surface has a capsule-shaped outer perimeter, with a seal-retaining wall extending perpendicularly about said backup surface perimeter; and a resilient seal interfitted with said seal-retaining wall, with said seal-retaining surface terminating at a forward wall, and said seal having a sealing surface extending forwardly of said forward wall.

12. A combination of an interface plate and a vacuum constriction device used with an elastic constriction ring, comprising:

a vacuum constriction device;

an interface plate comprising an interface plate member;

said interface plate member having an inner wall;

said inner wall being cylindrical and having an open, circular first end;

said first end intersecting a planar backup surface perpendicular to said inner wall, such that said first end defines a circular aperture in said backup surface; and retainer ring means adapted to hold an elastic constriction ring, said retainer means cooperating with said circular aperture to prevent the formation of abdominal and scrotal bulges past the elastic constriction ring when vacuum is applied to the vacuum constriction device;

wherein said interface plate member is an integral part of said vacuum constriction device.

* * * * *